(12) United States Patent
Hauschulte

(10) Patent No.: US 10,709,519 B2
(45) Date of Patent: Jul. 14, 2020

(54) SURGICAL LAMP HAVING CONTROL

(71) Applicant: TRILUX MEDICAL GMBH & CO. KG, Arnsberg (DE)

(72) Inventor: Hermann Hauschulte, Arnsberg (DE)

(73) Assignee: TRILUX MEDICAL GMBH & CO. KG, Arnsberg (DE)

( * ) Notice: Subject to any disclaimer, the term of this patent is extended or adjusted under 35 U.S.C. 154(b) by 287 days.

(21) Appl. No.: 14/910,562

(22) PCT Filed: Aug. 5, 2014

(86) PCT No.: PCT/EP2014/066819
§ 371 (c)(1),
(2) Date: Jun. 15, 2016

(87) PCT Pub. No.: WO2015/018830
PCT Pub. Date: Feb. 12, 2015

(65) Prior Publication Data
US 2016/0270873 A1    Sep. 22, 2016

(30) Foreign Application Priority Data
Aug. 5, 2013 (DE) ..................... 10 2013 215 337

(51) Int. Cl.
*A61B 90/30* (2016.01)
*H05B 47/105* (2020.01)

(52) U.S. Cl.
CPC ........... *A61B 90/30* (2016.02); *H05B 47/105* (2020.01)

(58) Field of Classification Search
CPC .................................................... A61B 90/30
See application file for complete search history.

(56) References Cited

U.S. PATENT DOCUMENTS 8,662,719 B2    3/2014 Rohwedder et al.
2011/0175551 A1    7/2011 Wood et al.
(Continued)

FOREIGN PATENT DOCUMENTS

CN    102374464    3/2012
DE    102008049526 A1    4/2010
(Continued)

OTHER PUBLICATIONS

PCT International Search Report and Written Opinion dated Feb. 2, 2015, received in corresponding PCT Application No. PCT/EP14/66819, 10 pgs.
(Continued)

*Primary Examiner* — Olivia C Chang
(74) *Attorney, Agent, or Firm* — Grossman, Tucker, Perreault & Pfleger, PLLC

(57) ABSTRACT

The invention relates to a surgical lamp (1) that can be controlled without contact, comprising a control unit and a sensor unit, wherein the control unit is designed to control the surgical lamp (1), wherein the sensor unit is designed to detect a motion of an action element and to convert said motion of the action element into motion data, wherein the control unit is designed to read out the motion data generated by the sensor unit and to control the surgical lamp (1) in dependence on the motion data. The sensor unit is designed in such a way that the sensor unit ensures the detection of the motion of the action element in three dimensions in a measurement space (3), which is arranged below the surgical lamp in an emission direction.

5 Claims, 1 Drawing Sheet

(56) References Cited

U.S. PATENT DOCUMENTS

Figure 1:
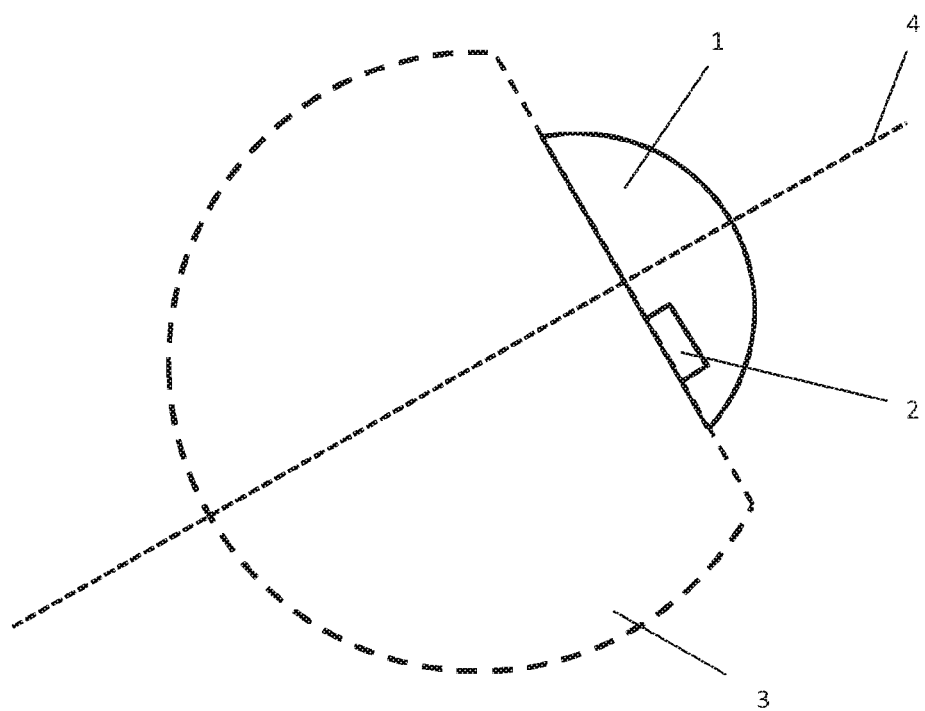

| | | | |
|---|---|---|---|
| 2012/0075832 A1 | 3/2012 | Schmid et al. | |
| 2012/0259178 A1 | 10/2012 | Kim et al. | |
| 2013/0111651 A1* | 5/2013 | Waters | A42B 1/004 2/209.13 |
| 2014/0191664 A1* | 7/2014 | Johnson | H05B 33/0857 315/152 |

FOREIGN PATENT DOCUMENTS

| | | |
|---|---|---|
| DE | 102010026319 A1 | 1/2012 |
| EP | 1728482 A1 | 12/2006 |
| EP | 2283790 A1 | 2/2011 |
| GB | 2423378 A | 8/2006 |
| WO | 2010146446 A1 | 12/2010 |

OTHER PUBLICATIONS

Office Action dated Nov. 15, 2017, received in related Chinese Application No. 201480051713.9.

* cited by examiner

SURGICAL LAMP HAVING CONTROL

The invention relates to a surgical lamp that can be controlled without contact, according to the preamble of claim 1.

Conventional surgical lamps (operating lamps) are used for illuminating an operation field where surgery is performed on a living body. Considering that surgery is performed on an open body, sterility in the operating room is of utmost importance. Particularly important is the avoidance of any contamination of the surgeon's hands and of the instruments used during the operation by viruses and bacteria. For this reason, utmost care is taken during an operation that the surgeon who performs the operation does not come into contact with unsterilized items.

Accordingly, it is also strictly avoided during an operation that the surgeon comes into contact with the surgical lamp which cannot be sterilized as such, except of the focusing handle. Here the problem arises that for performing the operation the operation field must be illuminated as best as possible by the surgical lamp and the illumination must be oriented according to the surgeon's needs with regard to the wound to be operated. It is advantageous, for example, if the light color, the light intensity, the direction in which light is emitted from the surgical lamp onto the operation field, and/or the size of the illuminated region, i.e. the focus of the surgical lamp, can be adjusted according to the surgeon's needs. These illumination characteristics of the surgical lamp can be usually set via the parameters of the surgical lamp, which then illuminates the illumination region in the operation field according to the settings. As the surgeon himself cannot control the non-sterile surgical lamp, except of the focus, and thus cannot control the surgical lamp so that the same has the radiation or illumination characteristics desired by the surgeon, the control of the surgical lamp must be carried out by other persons who are not directly involved in the operation and thus cannot contribute to a contamination of open wounds on the body as a consequence of a contamination via the surgical lamp. Accordingly, in practice, the surgeon is required to instruct this person in controlling the surgical lamp and cannot perform the control of the surgical lamp himself. In practice, this is problematic, above all because of the various surgical situations which may occur during an operation, each of which requiring a different illumination of the operation field. The surgeon is required to explain his changing needs concerning the illumination characteristics of the surgical lamp to the persons controlling the surgical lamp and making the adjustments, which frequently leads to time delays during the operation and to an illumination of the operation field which is not optimal.

In prior art, this problem is addressed by arranging a control unit and a sensor unit on the surgical lamp, wherein the sensor unit communicates with said control unit. The sensor unit is covered with a sterile cover that does not affect the functioning of the sensor unit. Accordingly, a sterile action element can be moved along the sterile cover of the sensor unit, whereby said sensor unit generates motion data. A hand or an instrument used during the operation can be used for example as an action element. The control unit reads out the motion data generated by the sensor unit and controls the surgical lamp in dependence on the read-out motion data. The control unit controls the surgical lamp depending on the motion the action element has performed on the cover of the sensor unit. The control of the surgical lamp can comprise for example the setting of parameters of the surgical lamp by which a radiation characteristic of the surgical lamp and hence an illumination characteristic of the surgical lamp in the operation field are set. For example, it is possible to provide the above-described illumination properties by a corresponding control via a corresponding setting of the parameters of the surgical lamp. By this control there can be adjusted for example the focus, especially the focus size of the surgical lamp and thus the size of the area of the illuminated region in the operation field, the light color of the light emitted from the surgical lamp, the intensity of the emitted light, the distance of the surgical lamp from the operation field and/or the emission direction in which the surgical lamp emits light onto the operation field. A corresponding advantageous surgical lamp is known from document EP 2 4342 02 A1.

Accordingly, the known surgical lamps ensure control of the surgical lamp without contact in the sense that only the sterile cover needs to be touched for controlling the surgical lamp so that the surgeon himself can perform that control. However, the known surgical lamps have various drawbacks. For example, for controlling the surgical lamp, the surgeon must move his hand towards the control unit and thus far away from the operation field, which the surgeon may consider as disturbing. For example, the surgeon is considerably distracted from the operation when he tries to reach the sterile cover in a targeted manner. For example, due to the small size of the sensor element by which the sensor unit can detect motions, a control of the surgical lamp by the surgeon is possible only to limited extent. For this reason, the surgeon must continue to rely on an additional person for controlling the surgical lamp. For example, due to the sterile cover, the sensor unit may be error-prone, which makes it more difficult or even impossible to generate motion data or motion data are distorted if the cover is not correctly installed.

It is an object of the invention to provide a surgical lamp that can be controlled without contact, particularly by the surgeon himself, and which can solve the above-described problems in known surgical lamps, at least partially.

As a solution of the above-described technical problem the invention proposes a surgical lamp with the features of claim 1. The surgical lamp according to the invention is characterized in that the sensor unit of the surgical lamp is configured to ensure a detection of the motion of the action element in three dimensions in a measurement space which is arranged below the surgical lamp in the emission direction of the surgical lamp, wherein the surgical lamp has a sleep mode in which the control unit ensures that there is no control of the surgical lamp via the read-out motion data, as well as an activated mode in which the control unit ensures the control of the surgical lamp via the read-out motion data, wherein the control unit is configured to switch from the sleep mode to the activated mode in response to an initialization action and to switch form the activated mode to the sleep mode in response to a deactivation action, wherein a defined initialization motion of the action element in the measurement space (3) is specified as the initialization action.

The surgical lamp according to the invention offers a plurality of advantages. As a result of the sensor unit being designed to ensure the detection of the motion of the action element in three dimensions, the sensor unit can respectively generate motion data for a huge number of different motions that can be performed three-dimensionally. These various motion data can be respectively read out by the control unit so that a comprehensive control of the surgical lamp and hence a setting especially of all relevant properties of the directional characteristic of the surgical lamp are possible by corresponding motions of the action element. In one embodiment, further control options can be provided by the sensor unit being designed for detecting motions of a multipart action element. In an exemplary embodiment, the action element can consist of two parts for example, such as two hands or two tools. For example, the sensor unit can be designed to detect the relative motion of the two parts of the action element to each other and to convert the relative motion into motion data, which can then be read out by the control unit. The detection of a relative motion of two parts of the action element can ensure a particularly precise generation of motion data and thus a particularly precise control of the surgical lamp by the control unit. In a different embodiment, the sensor unit is designed to detect the motion sequence of the action element in the sense that the sensor unit generates motion data that reflect the translocation of the action element during the motion. In a further embodiment, the control unit can be designed to detect the speed and/or acceleration of the action element and to include these in the generation of the motion data. It is also possible to combine features of the above-mentioned embodiments.

For implementing a sensor unit that allows the detection of three-dimensional motions in the measurement space, the person skilled in the art can resort to known constructions of sensor units. For example, the sensor unit can consist of a leap sensor or a 3D camera. For example, the sensor unit can consist of several cameras, which are spatially offset and thus enable a three-dimensional detection of motions within a measurement space. For example, the sensor unit can consist of several leap sensors. For example, the sensor unit can consist of several infrared sensors, which are spatially offset in such a manner that a three-dimensional detection of an action element having a particular temperature is possible in the measurement space. For example, the sensor unit can comprise one and especially more than one and especially various sensor elements of the described sensor elements or of other sensor elements such as a leap sensor, a 3D camera, and an infrared sensor.

As described above, the surgical lamp according to the invention is characterized in that the motions in a measurement space that is arranged below the surgical lamp in the emission direction can be detected via the senor unit. Accordingly, the measurement space extends between the surgical lamp and the operation field. Therefore, the surgeon does not have to move his hand far away from the operation field for controlling the surgical lamp. In one embodiment, the operation field itself is located within the measurement space. In another embodiment, the operation field is spaced from the measurement space in the emission direction and is located below the measurement space. Therefore, for carrying out the motion for controlling the surgical lamp, the surgeon merely has to move his hand into the measurement space, which is located between the surgical lamp and the operation field and thus near the operation field, as has been described. Preferably, the measurement space of the surgical lamp is arranged that close to the operation field that the surgeon can move his hand in the measurement space while remaining in his operating position and merely moving his arm and/or hand. Preferably, the measurement space is dimensioned sufficiently large for the surgeon to perform the said motions in the measurement space, without having to concentrate closely on such motions because of a considerable spatial limitation.

For example, the measurement space can be spaced from the optical axis in a direction vertical to the optical axis of the surgical lamp. The optical axis of the surgical lamp is defined as a straight line passing through the center of the area in which light is emitted from the surgical lamp in the emission direction. This will ensure for example that the sensor unit does not detect a movement of the surgeon within the operation field illuminated by the surgical lamp so that a possibly undesired control of the surgical lamp is not performed by accident in response to a movement of the surgeon. In a preferred embodiment, an optical axis along which light is emitted from the surgical lamp passes through the measurement space. This embodiment brings the advantage that the surgeon can perform a control of the surgical lamp by moving his hand within the area illuminated by the surgical lamp so that the surgeon has to move only very little from his operating position. In an advantageous embodiment, the sensor unit is constructed in such a manner that it ensures a three-dimensional motion of the action element in a measurement space having a volume of 1 $m^3$. When choosing the dimension of the measurement space, care is taken to ensure that the measurement space has a dimension that is convenient for the surgeon. In a preferred embodiment, the measurement space is arranged symmetrically around the optical axis in a plane perpendicular to the optical axis. Taking into account the definition of the optical axis used in the description of the invention, the definition being that the optical axis extends in the emission direction of the surgical lamp and through the center of the area into which light is emitted from the surgical lamp, the described preferred embodiment ensures that the surgeon can be certain that his movements are detected by the sensor unit if they are performed within the area illuminated by the operating lamp. In this manner the surgeon can make sure rather easily that the movements he makes are detected.

In an advantageous embodiment, the sensor unit includes precisely one sensor that is arranged at a sensor position on the surgical lamp, the measurement space being symmetrical around the sensor position. In particular, the measurement space can be in the form of a cylinder and the sensor position can be in the center of the basic area of the cylinder. In particular, the measurement space can be in the form of a spherical section and the sensor position can be in the center of the basic area of the spherical section. The sensor is designed corresponding to the implementation of the measurement space. The advantageous embodiment can bring the benefit that with only one sensor a measurement space can be ensured which is located and has a dimension such as to guarantee an especially good control of the surgical lamp. To this end, especially the sensor position can be fixed as required. The advantageous embodiment allows an inexpensive production of a precisely controllable surgical lamp.

In a preferred embodiment, the surgical lamp has a sleep mode in which the control unit ensures that there is no control of the surgical lamp via the read-out motion data, and it has a activated mode in which the control unit ensures control of the surgical lamp via the read-out motion data, the control unit being designed in such a manner that switching from the sleep mode to the activated mode can be effected by an initialization action and switching from the activated mode to the sleep mode can be effected by a deactivation action. Accordingly, a control of the surgical lamp by motion is not possible during the sleep mode.

For example, the surgical lamp can be constructed in such a manner that during the sleep mode the control unit does not read out motion data generated by the sensor unit. For example, the surgical lamp can be constructed in such a manner that during the sleep mode the control unit does not detect motions and thus does not generate motion data. In one embodiment, the control unit reads out the motion data during the sleep mode, but does not perform a control in dependence on the read-out motion data. On the other hand, during the activated mode, a control of the surgical lamp via a motion within the measurement space can be performed. In a corresponding manner, during the activated mode of the surgical lamp, the sensor unit detects a motion of the action element in the measurement space and the control unit controls the surgical lamp in dependence on the motion data the control unit has read out from the sensor unit.

For example, the initialization action can consist in an operation of the surgical lamp. For example, the initialization action can consist in the action of operating a switch at the surgical lamp for switching the surgical lamp to the activated mode. In a corresponding manner, the deactivation action can consist in the action of operating a switch for causing switching from the activated mode to the sleep mode. The initialization action and the deactivation action can each comprise also several actions, for example a predetermined motion in the measurement space and/or a predetermined proximity of the action element to the sensor unit and/or a predetermined motion. For example, the initialization action can comprise a predetermined combination of actions. In particular, the deactivation action can also consist in that no motion of the action element within the measurement space is performed during a particular dead time, which automatically causes switching from the activated mode to the sleep mode.

In an advantageous embodiment, an initialization motion of the action element in the measurement space is specified as an initialization action. In this embodiment for example, the surgical lamp can be constructed in such a manner that switching from the sleep mode to the activated mode is achieved only by performing a predetermined specified motion in the measurement space. For example, as an initialization motion there can be determined that the action element is moved two times vertically to the optical axis within the measuring space at a speed higher than a predetermined minimum speed. For example, via a correspondingly set minimum speed there can be specified as an initialization motion that two parts of an action element, for example two hands, are quickly mutually crossed. It is particularly advantageous to determine the initialization motion in such a manner that the detection of the relative motion of the action element is possible during the motion. In this manner it can be achieved that the sensor unit reliably detects the initialization motion even if the sensor unit is not suitable for the detection of an absolute position of the action element in the measurement space.

In one embodiment, the sensor unit always generates motion data also during the sleep mode. In one embodiment, the sensor unit generates motion data also during the sleep mode, in dependence on a motion of the action element in the measurement space, and the control unit reads out said motion data also during the sleep mode while it does simply not control the surgical lamp during the sleep mode. On performing an initialization motion, the same is detected by the sensor unit and read out by the control unit whereby the control unit is activated for controlling the surgical lamp.

In a preferred embodiment, the surgical lamp is constructed in such a manner that the control unit controls the surgical lamp only in dependence on such motion data generated by the sensor unit for the motions of the action element that has completed the initialization motion. It can be excluded in this manner that a control of the surgical lamp is performed through the motion of an element in the measurement space which is not the action element.

This avoids an undesired control of the surgical lamp by an accidental motion of an element in the measurement space. In an embodiment, in which the action element has a two-part design, the initialization motion can consist in a relative motion of said two parts of the action element against each other, whereupon the sensor unit only detects motions of said two parts of the action element and coverts these motions into motion data thus enabling a control through said two parts of the action element. In this case, the sensor in cooperation with the control unit tracks the motions of the action element after the completion of the initialization motion. For example, it can be provided that after the initialization motion a certain pause time, for example 2 seconds, must be provided before a control of the surgical lamp via a motion of the detected action element can be performed.

In a further preferred embodiment there is specified as a deactivation action that no motion of the action element has been detected during a predetermined dead time. Accordingly, switching from the activated mode to the sleep mode is easily possible by the action element resting in the measurement space or not performing any motion in the measurement space during said dead time. In a different embodiment there is specified as a deactivation action a deactivation motion of the action element in the measurement space. The deactivation motion can be determined in the same manner as described above for the initialization motion.

In one embodiment, the sensor unit of the surgical lamp is adapted for detecting motions of precisely one action element at a time, wherein the sensor unit uninterruptedly detects the motion of the action element until that motion is completed and ensures the detection of another action element after a predetermined rest period of the action element. This makes sure that motion data are not inadvertently generated by the control unit which are based on the motion of an element in the measurement space which does not correspond to the action element with which a person, especially the surgeon, intends to achieve control of the surgical lamp. Additionally, this can ensure that after respecting a predetermined rest period, for example 3 seconds, switching from one action element to another action element can take place so that after a control of the surgical lamp by a first action element the control of the surgical lamp by a second action element is possible. For example, this can be advantageous in a case where the surgeon has made a first hand movement with one hand for performing a first control action of the surgical lamp and thereafter is unable to move this hand for reasons of surgery, but can use his other hand for performing a second control action of the surgical lamp. In one embodiment, in which there is specified as a deactivation action that any motion of the action element has not been detected during a preset dead time, the rest period can be fixed to a lower value than the dead time so that switching from one action element to another action element is possible before the surgical lamp switches from the activated mode to the sleep mode.

In one embodiment, the surgical lamp comprises a display element displaying a state of readiness of the surgical lamp or of the sensor unit of the surgical lamp for the detection of said other action element. In this manner, the surgeon can learn from this display element whether a control of the surgical lamp via said other action element is possible.

Further, it can be advantageous for the surgical lamp to comprise a display unit indicating whether a control of the surgical lamp through a motion of the action element is possible. For example, said display unit can indicate whether the surgical lamp is in a activated mode. For example, a corresponding indication of the display unit can be made by the emission of an audible alarm when the surgical lamp is in the activated mode. For example, the display unit can comprise an indicator light, which lights up when the surgical lamp is in the activated mode. For example, the display unit can include an indicator light, which lights up in a first color when the surgical lamp is in the sleep mode and in a second color when the surgical lamp is in the activated mode. In one embodiment, the display element is incorporated in the display unit so that the display unit also performs the function of the display element. The indication through the display element can take place in the same manner as previously described in the context of the indication through the display unit.

Figure 2:
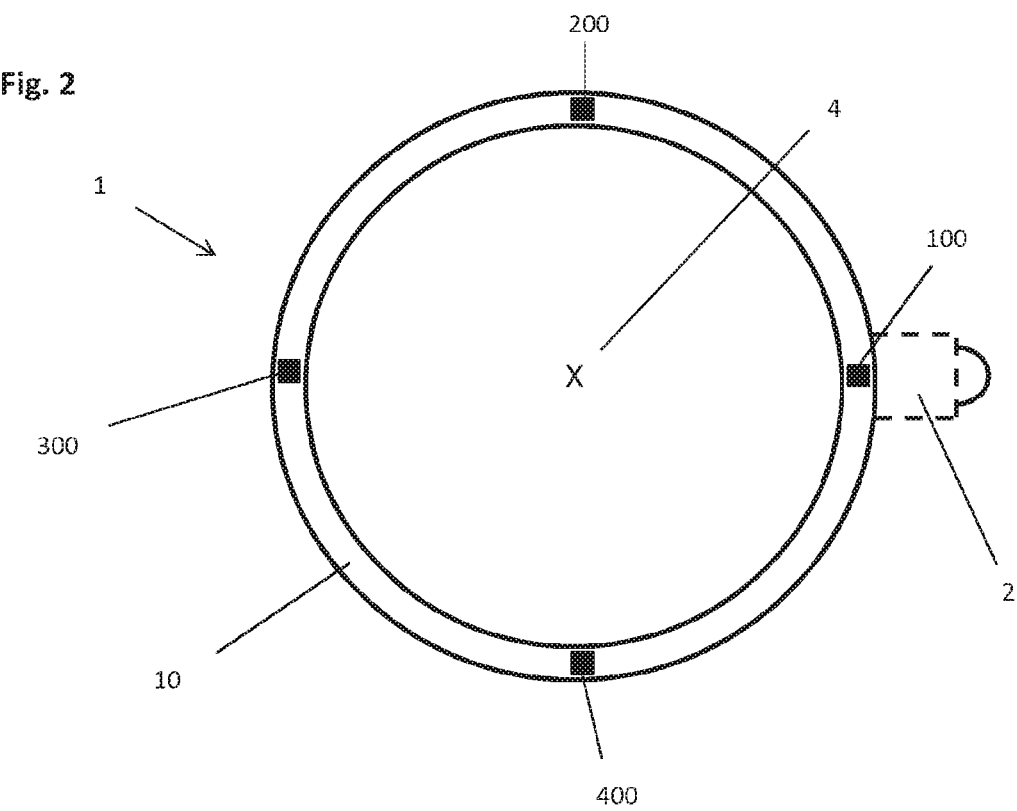

The invention will now be described in more detail with reference to two drawing Figures, wherein it is shown by FIG. 1 a schematic representation of a surgical lamp according to the invention in a lateral view;

FIG. 2 a schematic representation of a surgical lamp according to the invention from below.

FIG. 1 schematically shows the lateral view of a surgical lamp 1 of the invention and schematically shows the measurement space 3, which is arranged below the surgical lamp 1 in the emission direction. Further indicated in FIG. 1 is the optical axis 4, which extends in the emission direction of the surgical lamp 1 and lies in the center of the area illuminated by the surgical lamp 1 in a plane which is perpendicular to the optical axis 4.

FIG. 1 merely shows a two-dimensional representation of the lateral view of the described embodiment of the surgical lamp 1 of the invention. The measurement space 3 is in the form of a spherical section. The sensor unit of the illustrated surgical lamp 1 of the invention includes a sensor 2 that is arranged at a lower rim of the surgical lamp 1 in the emission direction and which is designed in such a way that it can detect motions of an action element in three dimensions in the illustrated measurement space 3. In the illustrated exemplary embodiment, a conventional leap sensor is used as a sensor 2. A conventional leap sensor is characterized in that it is suitable for detecting three-dimensional motions with high precision. In one embodiment, said leap sensor comprises two cameras suitable for recording in the infrared range and three infrared LEDs. The components of the leap sensors are controlled in such a manner that the cameras are read-out very frequently so that the leap sensor can make a determination of the position of an element to be monitored usually more than 200 times per second. In addition, a conventional leap sensor allows an accurate determination of the position of elements in a measurement space of approx 0.8 m$^3$, which substantially has the form of a spherical section. This ensures a very precise control of the surgical lamp 1 in a surgical lamp 1 according to the invention including a leap sensor as the sensor 2. In other embodiments other sensor types may also ensure a correspondingly precise control of the inventive surgical lamp.

In the present embodiment, the sensor 2 of the sensor unit of the surgical lamp 1 is fixed to the frame of the surgical lamp 1. The active sensor elements of the sensor 2 are oriented in such a way that that the sensor 2 can detect three-dimensional motions in the measurement space 3 located below the surgical lamp 1 and can generate motion data corresponding to the motions. In the present embodiment, said measurement space has a length of approx 1100 mm, a diameter of approx 1000 mm and hence a volume of approx 0.9 m$^3$. In other embodiments also other geometrical forms of the measurement space and other volumes, e.g. from 0.6 to 1 m$^3$, can be provided. The base of the measurement space 3 which extends perpendicularly to the optical axis 4 can for instance have the form of a circle, as in the present embodiment, the form of a square or the form of another polygon.

The described surgical lamp 1 according to the invention is constructed in such a way that a surgeon can control the surgical lamp 1 by motions as soon as he performs the motions with an action element in the measurement space 3, i.e. as soon as he moves an action element in a corresponding proximity to the surgical lamp 1 below the surgical lamp 1. In the present embodiment, predetermined parameters (setting parameters) for the surgical lamp 1 assigned to correspondingly predetermined motion data are stored in the control unit (not shown in FIG. 1) of the surgical lamp 1. The control unit compares motion data it reads out from the control unit to said stored motion data and, if read-out motion data correspond to stored motion data, controls the surgical lamp 1 corresponding to the setting parameters that are stored for the corresponding motion data. A corresponding assignment of motion data and parameters and a corresponding comparison of motion data can also be implemented in other exemplary embodiments.

In the control unit of the described surgical lamp 1 it is stored that only one hand or several hands are accepted as an action element. Corresponding requirements for a compulsory action element can be fixed in a different way in different embodiments. For example, a certain marking may be required, e.g. via an RFID, for an action element to be accepted for controlling the surgical lamp and for motion data to be generated from motions of said action elements. A corresponding requirement for an action element stored in the control unit may bring the benefit that any inadvertent control of the surgical lamp 1 via moving elements can be excluded. For example, a surgeon's glove can be provided with a corresponding marking that has to be detected by the sensor unit in order that motion data are generated from the motion of the action element provided with said marking, in the described embodiment the glove carrying the marking. In an embodiment, which is not illustrated, a particular marking must be detected by the sensor unit for the activation action causing switching from the sleep mode to the activated mode of the surgical lamp 1.

In the present embodiment, provided that a hand is used as an action element, the following assignment of motion data to a predetermined control, especially to setting parameters, is stored: If motion data are read out that represent a movement of the hand along the optical axis 4 and towards the surgical lamp 1, the intensity of the light emitted from the surgical lamp 1 is reduced. In the case of motion data that represent a corresponding movement of the hand away from the surgical lamp 1, the illumination intensity is correspondingly increased. The quantity of the increase or reduction of the intensity corresponds to the distance the hand travels along the optical axis 4. It is further stored that the diameter of the area illuminated by the surgical lamp 1 is reduced when a movement is detected that corresponds to the movement of the thumb and index finger of the hand when said thumb and index finger are moved from the spread state towards each other to form a closed circle. In a corresponding manner it is stored that the diameter of the illuminated area is increased when a movement is detected where the hand's thumb and index finger form a circle that is opened by spreading the thumb and the index finger. It is further stored that the surgical lamp 1 switches from a sleep mode to a activated mode when two hands are detected in the measurement space 3 and when it is detected that both hands cross each other coming from outside. In a corresponding manner it is stored that the surgical lamp 1 switches from the activated mode to the sleep mode when two mutually crossed hands are moved away from each other. It is further stored that a first color temperature of light emitted from the surgical lamp is set when the thumb is detected, a second color temperature is set when the index finger is detected, a third color temperature is set when the middle finger is detected, and a fourth color temperature is set when the ring finger is detected. In other embodiments, motion data assigned to additional motions can be assigned to additional setting parameters of the surgical lamp 1.

FIG. 2 shows the surgical lamp 1 according to the invention shown in FIG. 1 in a lateral view in a schematic representation from below. In FIG. 2 the frame 10 of the surgical lamp 1 can be seen. The optical axis 4 extends into the drawing plane and is arranged in the middle of the frame 10 of the surgical lamp 1 in said drawing plane which is perpendicular to the optical axis 4. The optical axis 4 passes through the point of intersection of the cross that is shown in FIG. 2.

The sensor 2 is arranged at the sensor position 100 on the frame 10 of the surgical lamp 1. In other embodiments (not shown) additional sensors 2 of the sensor unit of the surgical lamp 1 can be arranged at additional sensor positions 200, 300 and/or 400. At an arrangement of sensors 2 of the sensor unit 2 on the frame 10 of the surgical lamp 1 it is particularly advantageous to arrange the sensors 2 to each other in such a way that always two sensors 2 are arranged mirror-symmetrically to each other, with the optical axis 4 being the mirror line. For example, if four sensors 2 are arranged at the sensor positions 100, 200, 300, and 400, which are thus equally spaced from the optical axis 4 and are respectively arranged offset to each by 90 degrees about the optical axis 4, an especially good spatial detection within the entire measurements space 3 is ensured. In particular, in a preferred embodiment, a sensor 2 can also be provided at a position along the optical axis, for example in a sterile handle of the surgical lamp. The arrangement of a sensor 2 along the optical axis can bring the advantage that the measurement space is arranged particularly advantageously and especially symmetrically to the optical axis relative to the area illuminated by the surgical lamp, allowing a particularly convenient control of the surgical lamp. In particular, this arrangement of a sensor 2 allows a particularly precise determination of the position and a detection of the motion of the action element near the operation field.

It is apparent from the described embodiments of the inventive surgical lamp 1 that a respective measurement space 3 is provided below the surgical lamp 1 in which motions of an action element for controlling the surgical lamp 1 can be detected. The dimension of the measurement space 3 can be dictated by the design of sensors 2 of the sensor unit. In particular, the dimension of the measurement space 3 can be chosen with view to particular requirements, which depend on the field of application of the surgical lamp.

LIST OF REFERENCE NUMBERS

1 surgical lamp
2 sensor
3 measurement space
4 optical axis
10 frame
100 sensor position
200 sensor position
300 sensor position
400 sensor position

What is claimed is:

1. A surgical lamp that is controllable without contact, comprising:
   a control unit and a sensor unit,
   wherein the control unit is configured to control the surgical lamp,
   wherein the sensor unit is configured to detect motion of an action element and to convert the motion of the action element into motion data which reflect a translation of the action element during the motion,
   wherein the control unit is configured to read out the motion data generated by the sensor unit and to control the surgical lamp in dependence on the motion data,
   wherein the sensor unit is configured to ensure a detection of the motion of the action element in three dimensions in a measurement space which is arranged below the surgical lamp in an emission direction,
   wherein the surgical lamp has a sleep mode in which the control unit ensures that there is no control of the surgical lamp via the read-out motion data, as well as an activated mode in which the control unit ensures the control of the surgical lamp via the read-out motion data,
   wherein the control unit is configured to switch from the sleep mode to the activated mode in response to an initialization action and to switch from the activated mode to the sleep mode in response to a deactivation action,
   wherein a defined initialization motion of the action element in the measurement space is specified as the initialization action, and
   wherein a non-detection of any movement of the action element during a predeterminable dead-time is specified as the deactivation action, and
   wherein the surgical lamp is configured such that a first predetermined motion of the action element provides the initialization motion, and, while in the activated mode and emitting light, another subsequent predetermined motion of the action element changes at least one of area, color and intensity of the light from the surgical lamp.

2. The surgical lamp according to claim 1, wherein an optical axis along which light is emitted from the surgical lamp passes through the measurement space.

3. The surgical lamp according to claim 2, wherein the measurement space is arranged symmetrically around the optical axis in a plane perpendicular to the optical axis.

4. The surgical lamp according to claim 1, wherein a further deactivation action is a defined deactivation motion of the action element in the measurement space.

5. The surgical lamp according to claim 4, wherein the sensor unit is constructed for detecting motions of precisely one action element at a time, wherein the sensor element uninterruptedly detects the motion of the action element until the completion of the motion and ensures the detection of another action element only after a predetermined rest period of the action element.

\* \* \* \* \*